(12) United States Patent
Maru

(10) Patent No.: US 10,426,749 B2
(45) Date of Patent: *Oct. 1, 2019

(54) SAFFLOWER OIL EMULSION AS DIETARY SUPPLEMENT AND PREPARATION THEREOF

(71) Applicant: INNOVITAMIN ORGANICS, LLC, Gainesville, FL (US)

(72) Inventor: Robert Maru, Livingston, NJ (US)

(73) Assignee: InnoVitamin Organics, LLC, Gainesville, FL (US)

(*) Notice: Subject to any disclaimer, the term of this patent is extended or adjusted under 35 U.S.C. 154(b) by 329 days.

This patent is subject to a terminal disclaimer.

(21) Appl. No.: 15/240,380

(22) Filed: Aug. 18, 2016

(65) Prior Publication Data
US 2016/0353784 A1 Dec. 8, 2016

Related U.S. Application Data

(62) Division of application No. 14/138,544, filed on Dec. 23, 2013, now Pat. No. 9,968,121, which is a division of application No. 13/213,534, filed on Aug. 19, 2011, now Pat. No. 8,623,433.

(60) Provisional application No. 61/430,596, filed on Jan. 7, 2011.

(51) Int. Cl.
| | | |
|---|---|---|
| A61K 31/201 | (2006.01) | |
| A23L 2/52 | (2006.01) | |
| A61K 36/286 | (2006.01) | |
| A23L 2/44 | (2006.01) | |
| A23L 29/10 | (2016.01) | |
| A23L 29/238 | (2016.01) | |
| A23L 29/25 | (2016.01) | |
| A23L 29/269 | (2016.01) | |
| A23L 29/30 | (2016.01) | |
| A23L 27/00 | (2016.01) | |
| A23L 27/30 | (2016.01) | |
| A23L 5/42 | (2016.01) | |
| A23L 5/44 | (2016.01) | |
| A23L 33/105 | (2016.01) | |
| A23L 33/115 | (2016.01) | |
| A23L 33/12 | (2016.01) | |
| A61K 9/00 | (2006.01) | |
| A61K 9/107 | (2006.01) | |
| A61K 47/10 | (2017.01) | |
| A61K 47/12 | (2006.01) | |
| A61K 47/22 | (2006.01) | |
| A61K 47/36 | (2006.01) | |

(52) U.S. Cl.
CPC .............. *A61K 31/201* (2013.01); *A23L 2/44* (2013.01); *A23L 2/52* (2013.01); *A23L 5/42* (2016.08); *A23L 5/44* (2016.08); *A23L 27/00* (2016.08); *A23L 27/30* (2016.08); *A23L 29/10* (2016.08); *A23L 29/238* (2016.08); *A23L 29/25* (2016.08); *A23L 29/27* (2016.08); *A23L 29/37* (2016.08); *A23L 33/105* (2016.08); *A23L 33/115* (2016.08); *A23L 33/12* (2016.08); *A61K 9/0095* (2013.01); *A61K 9/107* (2013.01); *A61K 36/286* (2013.01); *A61K 47/10* (2013.01); *A61K 47/12* (2013.01); *A61K 47/22* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 3,764,347 A | * | 10/1973 | Katz ................. | A23L 27/60 426/271 |
| 4,490,400 A | * | 12/1984 | Duncan .............. | A23L 27/63 426/335 |
| 4,678,808 A | | 7/1987 | Ward | |
| 4,794,015 A | | 12/1988 | Fujita | |
| 5,314,706 A | | 5/1994 | Colarow | |
| 5,624,698 A | * | 4/1997 | Dake ................. | A23L 2/38 426/330.3 |
| 2004/0013722 A1 | * | 1/2004 | Yang ................. | A61K 8/49 424/456 |

(Continued)

FOREIGN PATENT DOCUMENTS

| | | | | |
|---|---|---|---|---|
| EP | 2124648 B1 * | 1/2017 | .............. | A23L 2/02 |
| JP | 2005154301 | 6/2005 | | |

(Continued)

OTHER PUBLICATIONS

Norris et al. Am J Clin Nutr 2009;90:468-76. (Year: 2009).*
"Glycerol". Web date: 2009 [Retrieved from the Internet on: Aug. 6, 2013]. Retrieved from: <URL: http://www.webmd.com/vitamins-supplennents/ingredientmono-4-Glycerol.aspx?activeIngredientId=4&activeIngredientName=GLYCEROL>. (Year: 2009).*
Goodman, M. "Earthbound Farm Health Salad" from The Earth-Bound Cook. USA. p. 48. (Year: 2010).*

(Continued)

*Primary Examiner* — Amy L Clark
(74) *Attorney, Agent, or Firm* — Brian S. Steinberger; Hilary F. Steinberger; Law Offices of Brian S. Steinberger, P.A.

(57) ABSTRACT

A safflower oil emulsion and method of preparation includes a safflower oil that is natural, non-genetically modified organism (GMO), expeller pressed, solvent free, linoleic fatty acid rich oil wherein the linoleic fatty acid content is in a range from approximately 70% to approximately 80% of the total safflower oil that is mixed with a purified water and a mixture of at least one of an emulsifier, a flavoring, a natural sweetener, a natural coloring agent, and a gum. The mixture is blended to provide a stable emulsion that has the rich taste of a nutritious fruit smoothie is useful as a dietary supplement, and increases metabolism to support a healthy weight management program.

18 Claims, No Drawings

(56) References Cited

U.S. PATENT DOCUMENTS

2008/0241082 A1  10/2008  Guth

FOREIGN PATENT DOCUMENTS

| JP | 2005154301 A | * | 6/2005 | | |
| WO | 2008022857 | | 2/2008 | | |
| WO | WO-2008022857 A1 | * | 2/2008 | ............... | A23L 2/02 |

OTHER PUBLICATIONS

Rreilly. "Tomato-Free 'Marinara' Sauce". Web publication date: Dec. 15, 2009. [Retrieved from the internet on: Dec. 15, 2009]. Retrieved from: <URL: https://www.glutenfreeandmore.com/recipe/tomato-free-marinara-sauce/>. (Year: 2009).*

Asp, et al., Time-Dependent Effects of Safflower Oil to Improve Glycemia, Inflammation and Blood Lipids in Obses Post Menoausal Women with Type 2 Diabetes: A Randomized, Double-Masked, Crossover Study, Clinical Nutrition, 2010, pp. 1-7.

Norris, et al., Comparison of Dietary Conjugated Linoleic Acid with Safflower Oil on Body Composition in Obese Postmenopausal Women with Type 2 Diabetes Mellitus, Am. J. Clin. Nutr., 2009, pp. 468-476, vol. 90.

Harris, et al., Omega-6 Fatty Acids and Risk for Cardiovascular Disease: A Science Advisory from the American Heart Association Nutrition Subcommittee of the Council on Nutrition, Physical Activity, and Metabolism; Council on Cardiovascular Nursing; and Council on Epidemiology and Prevention, Journal of the American Heart Association, 2009, pp. 902-907.

Kris-Etherton, et al., The Debate About N-6 Polyunsaturated Fatty Acid Recommendations for Cardiovascular Health, American Dietetic Association, 2010, pp. 201-204.

Linoleic Acid and Safflower Oil: Two Dietary Oils Proven to Burn Fat, retrieved on Nov. 10, 2010; retrieved from http://www.weightlosstriumph.com/linoleic-acid-and-safflower-oil-two-dietary-oils-prov . . . , 4 pages.

Safflower Oil Important to Reaching Weight Loss Goals, retrieved on Nov. 10, 2010, retrieved from http://www.associatedcontent.com/article/2530561/safflower_oil_important_to_reaching . . . , 2 pages.

Safflower Oil: Lose Fat and Build Muscles, retrieved on Nov. 10, 2010, retrieved from http://www.associatedcontent.com/article/2171511/safflower_oil_lose_fat_and_build_mu . . . , 2 pages.

Glycerol, 2009, retrieved on Aug. 6, 2013, retrieved from http://www.webmd.com/vitamins-supplements/ingredientmono-4-GLYCEROL.aspx?activeIngredientId=4&activeIngredientName=GLYCERL>, 1 page.

Oelke, et al., Safflower, 2008, retrieved on Dec. 6, 2012, retrieved from http://web.archive.org/web/20080511172455/http://www.hort.purdue.edu/newcrop/afcm/safflower.html, 7 pages.

* cited by examiner

SAFFLOWER OIL EMULSION AS DIETARY SUPPLEMENT AND PREPARATION THEREOF

This application is a Divisional of U.S. patent application Ser. No. 14/138,544 filed Dec. 13, 2013, now U.S. Pat. No. 9,968,121, which is a Divisional of U.S. patent application Ser. No. 13/213,534 filed Aug. 19, 2011, now U.S. Pat. No. 8,623,433, which claims priority based on U.S. Provisional Application Ser. No. 61/430,596 filed on Jan. 7, 2011, the content of which is incorporated herein by reference. The entire disclosures of each of the applications listed in this paragraph are incorporated herein by specific reference thereto.

FIELD OF THE INVENTION

The present invention relates generally to the processing of safflower oil for a dietary supplement, and more specifically, to methods and systems and compositions for the production of dietary supplements with emulsified safflower oil.

BACKGROUND AND PRIOR ART

Safflower oil is a type of vegetable oil that is becoming increasingly popular among people who are very conscious about health. Safflower oil, as the name suggests, is a form of oil that is taken from the seeds of the safflower plant. There are two ways in which safflower oil is extracted from the plant, a chemical process and a mechanical process.

During the chemical process, the oil is refined by adding certain chemicals into it. This process actually eliminates the essential nutrients found in the oil and also contaminates it with certain harmful chemicals which can cause negative effects on the body when consumed. The other method of extracting oil from the safflower seeds is the mechanical method. In this method, instead of using chemicals, oil is taken from the plant by using a natural expeller also referred to as cold pressed. This is a better method than the former one, because it helps in retaining all the naturally found ingredients in safflower oil. Due to this reason, consumers should check the label well before buying safflower oil to know the method used for making the oil.

The essential ingredients present in safflower oil include, but are not limited to, phytosterols, saturated fat, monounsaturated fat, polyunsaturated fat, omega-6 fatty acids, vitamin E (Alpha Tocopherol), vitamin K and choline.

Safflower oil has the highest source of polyunsaturated fats found in any other type of vegetable oil, i.e. almost 79% polyunsaturated fatty acids (linoleic acid). It also contains 13 percent of monounsaturated fatty acids (oleic acid) and only 8% of saturated fatty acids. The other essential nutrients present in safflower oil are omega-6 fatty acids, cis-linoleic acid, vitamin E, and the like. Due to the presence of these ingredients in safflower oil, this oil is said to have various benefits to the health of individuals. It is important to note that most commercially sold safflower oil is designed for cooking and is a monounsaturated form containing high levels of oleic versus linoleic fatty acid.

This invention provides a dietary supplement containing safflower oil with a high level, i.e., greater than 70%, of linoleic polyunstaurated fatty acid.

Safflower Oil Health Benefits

As safflower oil contains high amounts of polyunsaturated fats, it helps in creation of prostaglandins in the human body. These hormone like compounds aid in strengthening the cell membranes and also in the proper functioning of the body.

According to, *Life Style Lounge: Health and Fitness* (http://lifestyle.iloveindia.com/lounge/health-benefits-of-safflower-oil-9614.html (Nov. 15, 2010)) one of the best health benefits of safflower oil is that it is an effective way of eliminating the excess fat accumulated in the body, thus aiding in weight loss. Brown fat is present in several areas of the body which is a major factor that aids in burning calories. Linoleic acid (LA) present in safflower oil is converted into gamma linoleic acid (GLA) that triggers the burning of calories by brown fat. Therefore, people who are looking for ways to lose as well as maintain their weight should include safflower oil in their regular diet.

Many doctors and dietitians recommend the use of safflower oil to obese people suffering from diabetes. Leigh E. Norris et al in "Comparison of Dietary Conjugated Linoleic Acid With Safflower Oil on Body Composition in Obese Postmenopausal Women with Type 2 Diabetes Mellitus," *The American Journal of Clinical Nutrition* (2009) 90 pages 468-476 reported on research conducted to find the benefits of safflower oil in older diabetic women who are overweight. These women were asked to take safflower oil supplements for a period of sixteen weeks, and the results were entirely positive. It was not only observed that they lost excess fat, but there was also a significant decline in their blood sugar levels.

The benefits reported by Leigh E. Norris et al in *The American Journal of Clinical Nutrition* (2009) supra are that the linoleic rich safflower oil lowered fasting glucose, improved insulin sensitivity, increased lean tissue mass and significantly reduced trunk (abdominal) adipose mass.

A study by Michelle L. Asp et al., "Time-dependent effects of safflower oil to improve glycemia, inflammation and blood lipids in obese, post-menopausal women with type 2 diabetes: A randomized, double-masked, crossover study" published in *Clinical Nutrition*, January 2011, pages 1-7, evaluates the metabolic effects of conjugated linoleic acid (CLA) and safflower (SFA) oils. Safflower oil (SAF) was chosen as a comparison treatment to CLA in the study with fifty-five post-menopausal, obese women with type 2 diabetes enrolled, and 35 women that completed this randomized, double-masked crossover study.

Treatments were 8 grams daily of conjugated linoleic acid (CLA) and 8 grams daily of safflower (SAF) oil for 16 weeks each. The participants were monitored to determine the earliest time that a significant effect was detected.

M. L. Asp et al. in *Clinical Nutrition*, supra reports that with regard to SAF, "we unexpectedly found a 6.3% decrease in fat mass of the trunk region." The analysis of additional data shows that consumption of SAF resulted in an increase in HDL cholesterol the "good" cholesterol, and an average decrease of 17.5% in C-reactive protein (CRP), a marker for systemic inflammation in the body; particularly in the arteries. High levels of CRP are associated with higher risk for heart conditions.

The M. L. Asp et al. study also found that participants consuming safflower oil (SAF) experienced a lowering of glycosylation, a process wherein sugar in the bloodstream attaches to the hemoglobin for the life of the red blood cells which is approximately 120 days. Hemoglobin A1c (HbA1c) is a test that measures insulin sensitivity over long periods of time. Insulin imbalance is directly tied to fat storage in the belly region.

In addition, the Asp et al. study reports that safflower oil (SAF) provided a significant decrease in fasting blood glucose. High glucose levels results in over production of insulin which has been linked to obesity.

During the 16 week Asp et al. study, conjugated linoleic acid (CLA) did not significantly alter the metabolic parameters including at least a 5% decrease in fat mass in the trunk region (belly fat), HDL cholesterol, fasting glucose, insulin sensitivity, C-reactive protein. However, the dramatic physiological effect of safflower oil (SAF) was unexpected and appreciated.

Apart from diabetic patients, using safflower oil, is an effective method of ameliorating premenstrual syndrome. Consuming safflower oil instead of hormonal drugs helps in regularizing menstrual cycles, thus getting rid of the problem of irregular periods, something which is very common in women these days due to various reasons.

Another benefit of using safflower oil is that it helps in the reduction of the level of cholesterol in the blood which reduces the risk of heart diseases in the individual. Apart from this, safflower oil is also said to strengthen the immune system of the body which increases its ability to resist the occurrence of certain infections as well as diseases.

Safflower oil also promotes hair growth and a healthy skin as it contains vitamin E. People who have dry, permed as well as colored hair are recommended to get a regular safflower oil massage for healthy looking hair. This odorless oil is mild and has a very light texture, and so easily absorbs into the scalp. People who are suffering from excess hair fall out can find effective hair regrowth with the application of safflower oil to the hair and scalp. Apart from benefiting the hair, there are also many safflower oil skin benefits. People who have dry skin should use safflower oil which helps in moisturizing the skin, especially during winter, thus making it smooth and healthy.

It is also recommended that people use safflower oil for acne treatment. Application of safflower oil on the skin helps to improve other skin problems like scars, wrinkles, etc., along with acne. Besides all of the above, safflower oil can also be used as a healthy cooking oil or as a dressing in salads.

It has also been shown that the consumption of organically grown vegetable oils increase the health of mammals over non-organic and processed foods or oils according to R. F. Edlich, et al. in "Revolutionary advances in organic foods," *Internal and Emergency Medicine*, (2007), 2:182.

Thus, it has become an important focus in science and medicine to include healthy fats in the diet of man and animals in the form of dietary supplements.

There remains great demand for high quality, bioavailable, effective dietary supplements. The current invention provides a high quality dietary supplement containing emulsified safflower oil and other all natural ingredients, such as green tea extract. The present invention maximizes the amount of high quality healthy fats and simultaneously increases the bioavailability of important nutrients to the consumer of the dietary supplement.

SUMMARY OF THE INVENTION

A primary objective of the invention is to deliver a novel emulsified form of high linoleic fatty acid content safflower oil in a dietary supplement form.

Another objective of the present invention is to improve the bioavailability of safflower oil processed for consumption by mammals so that the body can absorb the linoleic acid and other nutrients in safflower oil easily and instantly.

A further objective of the present invention is to use manufacturing procedures which allow for greater absorption of safflower oil nutrients.

Another objective of the present invention is to use manufacturing procedures that provide predigested, stable safflower oil emulsion of a creamy consistency that is shelf-stable with no separation for approximately eighteen months.

Another objective of the present invention is to provide emulsified safflower oil with added metabolism enhancing ingredients for additional weight loss benefits.

Another objective of the present invention is to use provide a dietary supplement that delivers all of the nutrient benefits of safflower oil in an all natural spoonable, pudding-like emulsion. This formula is free of artificial flavors, colors, sweeteners and has no added sugar. It is also soy and gluten free.

A preferred safflower oil dietary supplement in the form of a stable emulsion can consist essentially of 100% all natural, non-genetically modified organism (GMO), expeller pressed, solvent free, linoleic fatty acid rich safflower oil wherein the linoleic fatty acid is in a range from approximately 70% to approximately 80% of the total safflower oil content, purified water, and a mixture (I) of at least one of an emulsifier, a flavoring, a natural sweetener, a natural coloring agent, and a gum wherein the safflower oil, water and mixture (I) is blended for a sufficient time to form a stable emulsion that requires no refrigeration and has a shelf-life of approximately 18 months.

The linoleic fatty acid content of the safflower oil can be approximately 78%.

The emulsifier can be a food grade emulsifier selected from the group consisting of gum Arabic, xanthan gum, guar gum, glycerine, and mixtures thereof.

The flavoring can be a natural fruit flavor. The natural sweetener can be selected from at least one of xylitol and glycerine. The natural sweetener can be void of added sugar.

The natural coloring agent can be a vegetable juice selected from the juice of at least one of beets and carrots.

The purified water can be selected from at least one of deionized water, distilled water and pharmaceutical grade water.

The stable emulsion can have a citrus flavor. The stable emulsion can have a fruit berry flavor.

A method for emulsifying safflower oil for use in dietary supplements to increase metabolism and support a healthy weight management program, can consist of the steps of selecting a blender having a variable speed, combining purified water with safflower oil having approximately 78% linoleic fatty acid, approximately 12.0% oleic fatty acid, approximately 6% palmitic fatty acid, and approximately 2.0% stearic fatty acid, adding an emulsifier while stirring at a slow speed, and increasing the blender speed for a period of time to form a stable, spoonable, emulsion with smooth mouth-feel.

The step of adding an emulsifier can include adding at least one of a flavoring, a sweetener, a natural coloring agent, and a gum. The flavoring can be a natural fruit flavor. The sweetener can be selected from at least one of xylitol, glycerine, and stevia. The emulsifier can be a food grade emulsifier selected from the group consisting of gum Arabic, xanthan gum, guar gum, glycerine, and mixtures thereof.

The natural coloring agent can be a vegetable juice selected from the juice of at least one of beets and carrots.

The gum can be selected from at least one of gum Arabic, xanthan gum and guar gum. The purified water can be selected from at least one of deionized water, distilled water and pharmaceutical grade water. The stable, spoonable emulsion can have a citrus flavor. The stable, spoonable emulsion can have a fruit berry flavor.

Further objects and advantages of this invention will be apparent from the following detailed description of a presently preferred embodiment, which is illustrated in the accompanying FIGURE.

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the method and system of the present invention.

"Emulsion" is used herein to mean a mixture of two or more immiscible liquids. One or more liquids make up a dispersed phase and one or more liquids make up a continuous phase; the boundary between the phases is called the interface.

"Emulsion stability" refers to the ability of an emulsion to resist change in its properties over time or resist separation into a dispersed phase and a continuous phase.

"Emulsifier" is a substance which stabilizes an emulsion by increasing its kinetic stability such that the dispersed phase and the continuous phase do not separate or break down. Stated another way, an emulsifier causes a mixture of two immiscible substances, like oil and water to stay mixed together in an inseparable combination.

"Oil" is defined in the present invention as any fatty compound that is immiscible in water and which is liquid at room temperature.

"Organic" is used herein to mean products that are grown free of pesticides and herbicides and allowed to mature naturally.

"Safflower" is a plant native to countries from Iran to India, North America and the Far East. Safflower oil is derived from seeds of safflower plants, which are members of the sunflower family. Safflower oil has been used to treat baldness, cholesterol blockage, essential fatty acid deficiency and hair loss. Safflower oil is also used as culinary oil. It contains linoleic acid and oleic acid; essential fatty acids needed by the body and obtainable only from food. Essential fatty acids control inflammation, blood clotting and brain development.

"Safslim" is a trademarked phrase to represent the technology disclosed by the present invention.

For the first time, the present invention provides a safflower oil emulsion rich in vital and essential fatty acids with the rich taste of a fruit smoothie that is nutritious, and increases metabolism to support a healthy weight management program.

While the process concept is a relatively simple one, there are a variety of issues that complicate implementation, such as, but not limited to, creating an inseparable, stable emulsion with a shelf-life of at least eighteen months and creating an inseparable stable emulsion with an additive such as green tea extract for enhanced health benefits.

The product of the present invention consists of 100% all natural, non-genetically modified organism (GMO), expeller pressed, solvent free, linoleic rich safflower oil as the main ingredient which can be prepared as a stable, spoonable emulsion for consumption.

Table I below shows the fatty acid composition of the safflower oil used in the present invention.

TABLE I

Safflower Oil-Fatty Acid Content

| Fatty Acid composition of Safflower Oil | % Range | Preferred % to Total |
|---|---|---|
| Linoleic | 70-80 | 78.4 |
| Oleic | 10-15 | 12.0 |
| Palmitic | 4.5-6.5 | 5.8 |
| Stearic | 1.0-3.0 | 2.0 |

The water used in the preparation of the emulsion herein is purified water which is potable and free of harmful chemicals or bacteria. The water used herein can be deionized water, distilled water or pharmaceutical grade water.

The emulsifier in the present invention is a mixture of gums and glycerine which are multifunctional ingredients. The gums include gum Arabic, xanthan gum and guar gum which also function as thickeners and stabilizers in the emulsion. Similarly, glycerine is included in the mixture and is a multifunctional ingredient functioning as a sweetener, thickener and emulsifier.

In addition, a high potency standardized extract of green tea, high in epigallocatechin gallate (EGCG), a key phytonutrient in green tea can be added for additional health benefits. Green tea extract benefits, include, but are not limited to, preventing fat accumulation, increasing metabolic rate and fat burning, decreasing body weight and dimensions, improving insulin resistance and providing antioxidant benefits.

A commercially available, green tea extract, sold under the trademark Sunphenon™ is acceptable as an added phytonutrient. The green tea extract is 100% all natural, pure, pesticide and herbicide free, caffeine free and standardized to 90+% EGCG content. Sunphenon™ is a trademark of Taiyo International with offices located in Minneapolis, Minn. Another suitable supplier of an acceptable green tea extract is DSM Nutritional Products, Parsippany, N.J.

The formula in Table II below is prepared so that each serving will supply one teaspoon (1 tsp) of safflower oil along with 90 milligrams (mg) of EGCG extract. The recommended dosage is based on body weight. Males and females weighing less than 150 lbs can consume one tablespoon (1 tbsp) daily for effective results. Males and females weighing 150 lbs and more can consume two tablespoons (2 tbsp) daily for effective results.

TABLE II

Formulation Ingredients

| Ingredient | Function |
|---|---|
| Water | Aqueous phase |
| Safflower oil (5.8% palmitic acid; 2.0% stearic acid, 12.0% oleic acid; 78.4% linoleic acid) | Essential fatty acid |
| Green Tea Extract (optional) | Phytonutrient, antioxidant, metabolism booster |
| Xylitol | Natural sweetener |
| Glycerine | Natural sweetener, thickener, emulsifier |
| Gum Arabic | Thickener |
| Natural flavors | Flavoring |
| Citric Acid | Natural preservative, flavoring |
| Xanthan gum | Thickener, emulsifier |
| Guar gum | Stabilizer, emulsifier |
| Vegetable juice | Natural color |
| Ascorbyl Palmitate | Natural Preservative, fat soluble vitamin C |

Other optional ingredients that may be added to enhance weight management may include:
Plant Oils
CLA—Conjugated Linoleic acid—Special mixed isomer form of linoleic acid derived from safflower oil.
MCT—Medium Chain Triglycerides—naturally ocurring fatty acids found in coconut oil.
GLA—Gamma Linolenic acid—from various plant sources such as evening primrose oil, borage oil, or hemp seed oil.
Herbal Extracts
Irvingia Gabonensis also known as African Mango Extract—which has been shown in studies to assist in weight management by balancing blood sugar levels and reducing fat storage.
Raspberry Ketones, an active ingredient found in raspberry fruit shown to help enhance fatty acid oxidation in clinical trials.
Fiber supplements, known to assist with satiety, hunger and appetite suppression include soluble fibers, such as, oat bran, and insulin.

The invention is further described, but not limited by Examples 1-4 below. The ingredients begin with the selection of a 100% all natural, non-genetically modified organism (GMO), expeller pressed, solvent free, linoleic rich safflower oil and are listed in Table III below:

TABLE III

INGREDIENTS AND WEIGHT PERCENT FORMULAS

| Ingredient | Weight Percent | | | |
|---|---|---|---|---|
| | *Ex. 1 | Ex. 2 | Ex. 3 | Ex.4 |
| 70-80% Linoleic acid Safflower oil | 33 | 33 | 33 | 33 |
| Deionized water | 18 | 18 | 18 | 17 |
| Xylitol | 16 | 16 | 16 | 16 |
| Glycerine | 16 | 16 | 16 | 16 |
| Gum Arabic | 4 | 4 | 5 | 4 |
| Xanthan gum | 2 | 2 | 1 | 2 |
| Guar gum | 1 | 1.5 | 1 | 1.5 |
| Beta-Carotene | — | 0.5 | — | 0.5 |
| Vegetable juice | — | — | 3 | — |
| Citric acid | 2.5 | 2.5 | 2.5 | 2.5 |
| Sorbic acid | 0.45 | 0.45 | 0.45 | 0.45 |
| Vitamin E (d-alpha tocopherol) | 0.025 | 0.025 | 0.025 | 0.025 |
| Natural Flavors | 7 | 6 | 4 | 6 |
| Ascorbyl Palmitate | 0.025 | 0.025 | 0.025 | 0.025 |
| Green tea extract (optional ingredient) | — | — | — | 1 |
| | 100 | 100 | 100 | 100 |

Formula
*Ex. 1 = Example 1;
Ex.2 = Example 2;
Ex. 3 = Example 3;
Ex. 4 = Example 4

Example 1—A Method of Preparing Safflower Oil Emulsion

A proprietary blend of 100% all natural, non-genetically modified organism (GMO), expeller pressed, solvent free, linoleic rich safflower oil is mixed with deionized water and a mixture of flavorings, sweeteners and emulsifiers before adding to a blender. The mixture of flavorings, sweeteners and emulsifiers may be adjusted by persons skilled in the art.

Ambient conditions were used for mixing the above ingredients; the temperature is in a range from approximately 21.1° C. (70 degrees F.) to approximately 25.0° C. (77 degrees F.) and the pressure is at 1 atmosphere.
Ingredients are blended at high speed until a stable emulsion is formed. The resulting emulsion is smooth, spoonable, with a creamy mouthfeel. One tablespoon of the safflower oil emulsion supplies approximately 5 grams of safflower oil and approximately 3.9 grams of linoleic acid in a pre-micronized solution that improves digestion and assimilation through the intestinal tract and into the bloodstream, allowing for maximum cellular bioavailability. The shelf-stable oil emulsion requires no refrigeration and has a shelf-life of approximately 18 months.

Example 2—Orange Smoothie

The process of Example 1 is used to blend the following ingredients: 100% all natural, non-genetically modified organism (GMO), expeller pressed, solvent free, linoleic rich safflower oil, deionized water, xylitol, glycerine, natural flavors, gum Arabic, citric acid, xanthan gum, guar gum, beta carotene (for color), sorbic acid, Vitamine E (a d-alpha tocopherol) and ascorbyl palmitate to ensure freshness.

Example 3—Berry Smoothie

The process of Example 1 is used to blend the following ingredients: 100% all natural, non-genetically modified organism (GMO), expeller pressed, solvent free, linoleic rich safflower oil, deionized water, xylitol, glycerine, gum Arabic, natural flavors, vegetable juice (for color), citric acid, xanthan gum, guar gum, sorbic acid, Vitamine E (a d-alpha tocopherol) and ascorbyl palmitate to ensure freshness.

Example 4—Safflower Oil Emulsion with Metabolic Boosting Herbal Ingredient

A proprietary blend of 100% all natural, non-genetically modified organism (GMO), expeller-pressed, solvent free, linoleic rich safflower oil is mixed with green tea extract, deionized water, and a mixture of flavorings, sweeteners and emulsifiers before adding to a blender. The mixture of flavorings, sweeteners and emulsifiers may be adjusted by persons skilled in the art. However, in this example, the following quantities and ingredients were mixed with the safflower oil, green tea extract and water:
Ambient conditions were used for mixing the above ingredients; the temperature is in a range from approximately 21.1° C. (70 degrees F.) to approximately 25.0° C. (77 degrees F.) and the pressure is at 1 atmosphere.
Ingredients are blended at high speed, with speeds varying based on batch size, until a stable emulsion is formed. The resulting emulsion is smooth, spoonable, with a creamy mouthfeel. One tablespoon of the safflower oil emulsion supplies approximately 5 grams of safflower oil, 3885 mg of linoleic acid, 863 mg of oleic acid, 324 mg of palmitic acid, and 108 mg of stearic acid in a pre-micronized solution that improves digestion and assimilation through the intestinal tract and into the bloodstream, allowing for maximum cellular bioavailability of all nutrients.
The emulsion of the present invention is packaged as a yogurt or smoothie-like dietary supplement and sold for consumption of one tablespoon per serving with recommended dosage of one serving twice a day based on body weight and condition being treated.

Example 5—Comparison of Solubility of Nutrients from Safflower Oil Emulsion Vs. Safflower Oil Solubility studies show that emulsified safflower oil of the present invention is more bioavailable. When safflower oil is emulsified, it is "pre-digested" and therefore easier to metabolize by the body when compared to non-emulsified safflower oils.

The present invention provides an all natural safflower oil emulsion rich in vital and essential fatty acids with the rich taste of a nutritious fruit smoothie that increases metabolism to support a healthy weight management program.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A drinkable dietary supplement for increasing metabolism in the form of a stable, spoonable, drinkable emulsion, wherein the dietary supplement consists of:
    a linoleic fatty acid rich safflower oil, wherein the linoleic fatty acid is in a range from approximately 70% to approximately 80% of the total safflower oil;
    purified water mixed with the linoleic fatty acid rich safflower oil to form a purified water-safflower oil mixture; and
    an emulsifier mixture added to the purified water-safflower oil mixture, wherein the combined emulsifier mixture and purified water-safflower oil mixture are blended under ambient conditions in a temperature range from approximately 21.1 degrees C. to approximately 25 degrees C. and at a pressure of one atmosphere to provide the dietary supplement having a smooth mouth-feel and a shelf-life of approximately 18 months.

2. The drinkable dietary supplement of claim 1, wherein the linoleic fatty acid rich safflower oil includes approximately 78% linoleic fatty acid, 12.0% oleic fatty acid, approximately 6% palmitic fatty acid, and approximately 2.0% stearic fatty acid.

3. The drinkable dietary supplement of claim 1, wherein the emulsifier mixture includes:
    at least one gum emulsifier; at least one flavoring; at least one sweetener; at least one coloring agent; and at least one preservative.

4. The drinkable dietary supplement of claim 3, wherein the emulsifier is a food grade emulsifier selected from the group consisting of gum Arabic, xanthan gum, guar gum, glycerine, and mixtures thereof.

5. The drinkable dietary supplement of claim 3, wherein the at least one flavoring includes a fruit flavor.

6. The drinkable dietary supplement of claim 3, wherein the at least one sweetener is selected from at least one of xylitol, glycerin, and stevia.

7. The drinkable dietary supplement of claim 3, wherein the at least one coloring agent is a vegetable juice selected from the juice of at least one of beets and carrots.

8. The drinkable dietary supplement of claim 3, wherein the at least one preservative is selected from the group consisting of ascorbyl palmitrate, citric acid, sorbic acid, and vitamin E.

9. The drinkable dietary supplement of claim 1, wherein the safflower oil is approximately 33 weight percent of the dietary supplement.

10. A drinkable dietary supplement for increasing metabolism in the form of a stable, spoonable, drinkable emulsion, wherein the dietary supplement consists of:
    a safflower oil for increasing metabolism, wherein the safflower oil comprises linoleic fatty acid in a range from approximately 70% to approximately 80%, an oleic fatty acid in a range from approximately 10% to approximately 15%, a palmitic fatty acid in a range from approximately 4.5% to approximately 6.5%, and a stearic fatty acid in a range from approximately 1.0% to approximately 3.0% of the total safflower oil;
    purified water mixed with the safflower oil to form a purified water-safflower oil mixture; and
    an emulsifier mixture added to the purified water-safflower oil mixture, wherein the combined emulsifier mixture and purified water-safflower oil mixture are blended under ambient conditions in a temperature range from approximately 21.1 degrees C. to approximately 25 degrees C. and at a pressure of one atmosphere to provide the dietary supplement having a smooth mouth-feel and a shelf-life of approximately 18 months.

11. The drinkable dietary supplement of claim 10, wherein the safflower oil includes approximately 78% linoleic fatty acid, 12.0% oleic fatty acid, approximately 6% palmitic fatty acid, and approximately 2.0% stearic fatty acid.

12. The drinkable dietary supplement of claim 10, wherein the emulsifier mixture includes: at least one gum emulsifier; at least one flavoring; at least one sweetener; at least one coloring agent; and at least one preservative.

13. The drinkable dietary supplement of claim 12, wherein the emulsifier is a food grade emulsifier selected from the group consisting of gum Arabic, xanthan gum, guar gum, glycerine, and mixtures thereof.

14. The drinkable dietary supplement of claim 12, wherein the at least one flavoring includes a fruit flavor.

15. The drinkable dietary supplement of claim 12, wherein the at least one sweetener is selected from at least one of xylitol, glycerine, and stevia.

16. The drinkable dietary supplement of claim 12, wherein the at least one coloring agent is a vegetable juice selected from the juice of at least one of beets and carrots.

17. The drinkable dietary supplement of claim 12, wherein the at least one preservative is selected from the group consisting of ascorbyl palmitrate, citric acid, sorbic acid, and vitamin E.

18. The drinkable dietary supplement of claim 10, wherein the safflower oil is approximately 33 weight percent of the dietary supplement.

* * * * *